(12) United States Patent
Sacktor

(10) Patent No.: US 7,605,119 B2
(45) Date of Patent: Oct. 20, 2009

(54) MEMORY ENHANCING PROTEIN METHOD

(75) Inventor: Todd C. Sacktor, Yonkers, NY (US)

(73) Assignee: The Research Foundation of State University of New York, Albany, NY (US)

( * ) Notice: Subject to any disclaimer, the term of this patent is extended or adjusted under 35 U.S.C. 154(b) by 102 days.

(21) Appl. No.: 10/879,967

(22) Filed: Jun. 29, 2004

(65) Prior Publication Data

US 2004/0247584 A1 Dec. 9, 2004

Related U.S. Application Data

(62) Division of application No. 09/839,073, filed on Apr. 20, 2001.

(60) Provisional application No. 60/198,802, filed on Apr. 20, 2000.

(51) Int. Cl.
*A61K 38/00* (2006.01)

(52) U.S. Cl. .......................................................... 514/2

(58) Field of Classification Search ........................ None
See application file for complete search history.

(56) References Cited

U.S. PATENT DOCUMENTS

2004/0247584 A1 12/2004 Sacktor
2005/0070565 A1 3/2005 Arnsten et al.

OTHER PUBLICATIONS

Barad et al. Society for Neuroscience Abstracts 24(1-2): p. 328, abstract No. 131.14 (1998).*

Thiam, et al., "Direct Evidence of Cytoplasmic Delivery of PKC-α, -ϵ and -ξ Pseudosubstrate lipopeptides: Study of Their Implication in the Induction of Apoptosis", *FEBS Letters*, vol. 459, pp. 285-290, (1999).

* cited by examiner

*Primary Examiner*—Michael Pak
(74) *Attorney, Agent, or Firm*—Scully, Scott, Murphy & Presser, P.C.

(57) ABSTRACT

The present invention provides methods and compositions for enhancing memory in animals, including humans by the administration of an effective amount of an atypical form of protein kinase C such as protein kinase M zeta (PKMζ) or protein kinase C iota/lambda.

4 Claims, 11 Drawing Sheets

A

Silver Stain kDa

97-

66-

◄PKMζ

FIGURE 3

```
                          10         20         30         40         50
Sense     : CCCGGGCCTGGAGACATGAGGAGGCAGGGATGTGAGGGGCGGGGGACAGG
Antisense : GGGCCCGGACCTCTGTACTCCTCCGTCCCTACACTCCCCGCCCCTGTCC 60         70         80         90        100
            ACAGCCGGCCTTCCGTTAAATATCTGCTCCTCGCGCTCGAGCCTCCCTGC
            TGTCGGCCGGAAGGCAATTTATAGACGAGGAGCGCGAGCTCGGAGGGACG 110        120        130        140        150
            CTATTGTCGGGGCCGGAGCGAAGCCGACGCAGCATCAGCTCGTCAACGGG
            GATAACAGCCCCGGCCTCGCTTCGGCTGCGTCGTAGTCGAGCAGTTGCCC 160        170        180        190        200
            AAGGAAGATGCCTCCCTGCACGCCCGCCGCGCACAGAGCATAAAGAATCT
            TTCCTTCTACGGAGGGACGTGCGGGCGGCGCGTGTCTCGTATTTCTTAGA 210        220        230        240        250
            GCGCTGAGGAGGCAGGAGAAGAAAGCCGAATCTATCTACCGCCGGGGAGC
            CGCGACTCCTCCGTCCTCTTCTTTCGGCTTAGATAGATGGCGGCCCCTCG 260        270        280        290        300
            CAGAAGATGGAGGAAGCTGTACCGTGCCAACGGCCACCTCTTCCAAGCCA
            GTCTTCTACCTCCTTCGACATGGCACGGTTGCCGGTGGAGAAGGTTCGGT 310        320        330        340        350
            AGCGCTTTAACAGGAGAGCGTACTGCGGTCAGTGCAGCGAGAGGATATNG
            TCGCGAAATTGTCCTCTCGCATGACGCCAGTCACGTCGCTCTCCTATANC 360        370        380        390        400
            GGCCTCGCGAGGCAAGGCTACAGGTGCATCAACTGCAAACTGCTGGTCCA
            CCGGAGCGCTCCGTTCCGATGTCCACGTAGTTGACGTTTGACGACCAGGT 410        420        430        440        450
            TAAGCGCTGCCACGGCCTCGTCCCGCTGACCTGCAGGAAGCATATGGATT
            ATTCGCGACGGTGCCGGAGCAGGGCGACTGGACGTCCTTCGTATACCTAA
Protein :                                                   M  D>

460        470        480        490        500
            CTGTCATGCCTTCCCAAGAGCCTCCAGTAGACGACAAGAACGAGGACGCC
            GACAGTACGGAAGGGTTCTCGGAGGTCATCTGCTGTTCTTGCTCCTGCGG
            S  V  M  P  S  Q  E  P  P  V  D  D  K  N  E  D  A>

510        520        530        540        550
            GACCTTCCTTCCGAGGAGACARATGGAATTGCTTACATTTCCTCATCCCG
            CTGGAAGGAAGGCTCCTCTGTYTACCTTAACGAATGTAAAGGAGTAGGGC
            D  L  P  S  E  E  T  X  G  I  A  Y  I  S  S  S  R>
```

FIGURE 6

```
        560        570        580        590        600
GAAGCATGACAGCATTAAAGACGACTCGGAGGACCTTAAGCCAGTTATCG
CTTCGTACTGTCGTAATTTCTGCTGAGCCTCCTGGAATTCGGTCAATAGC
  K  H  D  S  I  K  D  D  S  E  D  L  K  P  V  I>

610        620        630        640        650
ATGGGATGGATGGAATCAAAATCTCTCAGGGGCTTGGGCTGCAGGACTTT
TACCCTACCTACCTTAGTTTTAGAGAGTCCCCGAACCCGACGTCCTGAAA
  D  G  M  D  G  I  K  I  S  Q  G  L  G  L  Q  D  F>

660        670        680        690        700
GACCTAATCAGAGTCATCGGGCGCGGGAGCTACGCCAAGGTTCTCCTGGT
CTGGATTAGTCTCAGTAGCCCGCGCCCTCGATGCGGTTCCAAGAGGACCA
  D  L  I  R  V  I  G  R  G  S  Y  A  K  V  L  L  V>
              <--ATP-Binding Site---------------

710        720        730        740        750
GCGGTTGAAGAAGAATGACCAAATTTACGCCATGAAAGTGGTGAAGAAAG
CGCCAACTTCTTCTTACTGGTTTAAATGCGGTACTTTCACCACTTCTTTC
  R  L  K  K  N  D  Q  I  Y  A  M  K  V  V  K  K>
--------------------ATP-Binding Site-------------->

760        770        780        790        800
AGCTGGTGCATGATGACGAGGATATTGACTGGGTACAGACAGAGAAGCAC
TCGACCACGTACTACTGCTCCTATAACTGACCCATGTCTGTCTCTTCGTG
  E  L  V  H  D  D  E  D  I  D  W  V  Q  T  E  K  H>

810        820        830        840        850
GTGTTTGAGCAGGCATCCAGCAACCCCTTCCTGGTCGGATTACACTCCTG
CACAAACTCGTCCGTAGGTCGTTGGGGAAGGACCAGCCTAATGTGAGGAC
  V  F  E  Q  A  S  S  N  P  F  L  V  G  L  H  S  C>

860        870        880        890        900
CTTCCAGACGACAAGTCGGTTGTTCCTGGTCATTGAGTACGTCAACGGCG
GAAGGTCTGCTGTTCAGCCAACAAGGACCAGTAACTCATGCAGTTGCCGC
  F  Q  T  T  S  R  L  F  L  V  I  E  Y  V  N  G>

910        920        930        940        950
GGGACCTGATGTTCCACATGCAGAGGCAGAGGAAGCTCCCTGAGGAGCAC
CCCTGGACTACAAGGTGTACGTCTCCGTCTCCTTCGAGGGACTCCTCGTG
  G  D  L  M  F  H  M  Q  R  Q  R  K  L  P  E  E  H>

960        970        980        990        1000
GCCAGGTTCTACGCGGCCGAGATCTGCATCGCCCTCAACTTCCTGCACGA
CGGTCCAAGATGCGCCGGCTCTAGACGTAGCGGGAGTTGAAGGACGTGCT
  A  R  F  Y  A  A  E  I  C  I  A  L  N  F  L  H  E>
```

FIGURE 6  (CONT'D)

```
          1010      1020      1030      1040      1050
       GAGGGGGATCATCTACAGGGACCTGAAGCTGGACAACGTCCTCCTGGATG
       CTCCCCCTAGTAGATGTCCCTGGACTTCGACCTGTTGCAGGAGGACCTAC
        R  G  I  I  Y  R  D  L  K  L  D  N  V  L  L  D>

1060      1070      1080      1090      1100
       CGGACGGGCACATCAAGCTCACAGACTACGGCATGTGCAAGGAAGGCCTG
       GCCTGCCCGTGTAGTTCGAGTGTCTGATGCCGTACACGTTCCTTCCGGAC
        A  D  G  H  I  K  L  T  D  Y  G  M  C  K  E  G  L>

1110      1120      1130      1140      1150
       GGCCCTGGTGACACAACGAGCACTTTCTGCGGAACCCCGAATTACATCGC
       CCGGGACCACTGTGTTGCTCGTGAAAGACGCCTTGGGGCTTAATGTAGCG
        G  P  G  D  T  T  S  T  F  C  G  T  P  N  Y  I  A>

1160      1170      1180      1190      1200
       CCCCGAAATCCTGCGGGGAGAGGAGTACGGGTTCAGCGTGGACTGGTGGG
       GGGGCTTTAGGACGCCCCTCTCCTCATGCCCAAGTCGCACCTGACCACCC
        P  E  I  L  R  G  E  E  Y  G  F  S  V  D  W  W>

1210      1220      1230      1240      1250
       CGCTGGGAGTCCTCATGTTTGAGATGATGGCCGGGCGCTCCCCGTTCGAC
       GCGACCCTCAGGAGTACAAACTCTACTACCGGCCCGCGAGGGGCAAGCTG
        A  L  G  V  L  M  F  E  M  M  A  G  R  S  P  F  D>

1260      1270      1280      1290      1300
       ATCATCACCGACAACCCGGACATGAACACAGAGGACTACCTTTTCCAAGT
       TAGTAGTGGCTGTTGGGCCTGTACTTGTGTCTCCTGATGGAAAAGGTTCA
        I  I  T  D  N  P  D  M  N  T  E  D  Y  L  F  Q  V>

1310      1320      1330      1340      1350
       GATCCTGGAGAAGCCCATCCGGATCCCCCGGTTCCTGTCCGTCAAAGCCT
       CTAGGACCTCTTCGGGTAGGCCTAGGGGGCCAAGGACAGGCAGTTTCGGA
        I  L  E  K  P  I  R  I  P  R  F  L  S  V  K  A>

1360      1370      1380      1390      1400
       CCCATGTTTTAAAAGGATTTTTAAATAAGGACCCCAAAGAGAGGCTCGGC
       GGGTACAAAATTTTCCTAAAAATTTATTCCTGGGGTTTCTCTCCGAGCCG
        S  H  V  L  K  G  F  L  N  K  D  P  K  E  R  L  G>

1410      1420      1430      1440      1450
       TGCCGGCCACAGACTGGATTTTCTGACATCAAGTCCCACGCGTTCTTCCG
       ACGGCCGGTGTCTGACCTAAAAGACTGTAGTTCAGGGTGCGCAAGAAGGC
        C  R  P  Q  T  G  F  S  D  I  K  S  H  A  F  F  R>
```

FIGURE 6 (CONT'D)

```
       1460       1470       1480       1490       1500
CAGCATAGACTGGGACTTGCTGGAGAAGAAGCAGGCGCTCCCTCCATTCC
GTCGTATCTGACCCTGAACGACCTCTTCTTCGTCCGCGAGGGAGGTAAGG
   S  I  D  W  D  L  L  E  K  K  Q  A  L  P  P  F>

1510       1520       1530       1540       1550
AGCCACAGATCACAGACGACTACGGTCTGGACAACTTTGACACACAGTTC
TCGGTGTCTAGTGTCTGCTGATGCCAGACCTGTTGAAACTGTGTGTCAAG
   Q  P  Q  I  T  D  D  Y  G  L  D  N  F  D  T  Q  F>

1560       1570       1580       1590       1600
ACCAGCGAGCCCGTGCAGCTGACCCCAGACGATGAGGATGCCATAAAGAG
TGGTCGCTCGGGCACGTCGACTGGGGTCTGCTACTCCTACGGTATTTCTC
   T  S  E  P  V  Q  L  T  P  D  D  E  D  A  I  K  R>

1610       1620       1630       1640       1650
GATCGACCAGTCAGAGTTCGAAGGCTTTGAGTATATCAACCCATTATTGC
CTAGCTGGTCAGTCTCAAGCTTCCGAAACTCATATAGTTGGGTAATAACG
   I  D  Q  S  E  F  E  G  F  E  Y  I  N  P  L  L>

1660       1670       1680       1690       1700
TGTCCACCGAGGAGTCGGTGTGAGGCCGCGTGCGTCTCTGTCGTGGACAC
ACAGGTGGCTCCTCAGCCACACTCCGGCGCACGCAGAGACAGCACCTGTG
   L  S  T  E  E  S  V>
----- C-terminus -->

1710       1720       1730       1740       1750
GCGTGATTGACCCTTTAACTGTATCCTTAACCACCGCATATGCATGCCAG
CGCACTAACTGGGAAATTGACATAGGAATTGGTGGCGTATACGTACGGTC 1760       1770       1780       1790       1800
GCTGGGCACGGCTCCGAGGGCGGCCAGGGACAGACGCTTGCGCCGAGACC
CGACCCGTGCCGAGGCTCCCGCCGGTCCCTGTCTGCAACGCGGCTCTGG 1810       1820       1830       1840       1850
GCAGAGGGAAGCGTCAGCGGGCGCTGCTGGGAGCAGAACAGTCCCTCACA
CGTCTCCCTTCGCAGTCGCCCGCGACGACCCTCGTCTTGTCAGGGAGTGT 1860       1870       1880       1890       1900
CCTGGCCCGGCAGGCAGCTTCGTGCTGGAGGAACTTGCTGCTGTGCCTGC
GGACCGGGCCGTCCGTCGAAGCACGACCTCCTTGAACGACGACACGGACG 1910       1920       1930       1940       1950
GTCGCGGCGGATCCGCGGGGACCCTGCCGAGGGGCTGTCATGCGGTTTC
CAGCGCCGCCTAGGCGCCCCTGGGACGGCTCCCCGACAGTACGCCAAAG
```

FIGURE 6 (CONT'D)

```
          1960       1970       1980       1990       2000
CAAGGTGCACATTTTCCACGGAAACAGAACTCGATGCACTGACCTGCTCC
GTTCCACGTGTAAAAGGTGCCTTTGTCTTGAGCTACGTGACTGGACGAGG 2010       2020       2030       2040       2050
GCCAGGAAAGTGAGCGTGTAGCGTCCTGAGGAATAAAATGTTCCGATGAA
CGGTCCTTTCACTCGCACATCGCAGGACTCCTTATTTTACAAGGCTACTT

AAAAAAAA
TTTTTTTT
```

FIGURE 6 (CONT'D)

MEMORY ENHANCING PROTEIN METHOD

CROSS-REFERENCE TO RELATED APPLICATION

This application is a divisional of U.S. application Ser. No. 09/839,073, filed Apr. 20, 2001, which claims priority from U.S. Provisional Application No. 60/198,802, filed Apr. 20, 2000.

FIELD OF THE INVENTION

The present invention provides methods for enhancing memory in animals, including humans. The present invention is also directed to methods for treating brain or spinal injury with the administration of an effective amount of atypical forms of protein kinase C, including protein kinase M zeta (PKMζ). The present invention further provides a method of inducing amnesia with the administration of an effective amount of a PKMζ inhibitor.

BACKGROUND OF THE INVENTION

A common working hypothesis for the physiological basis of memory is that persistent changes in behavior are mediated by long-term modifications in the strength of synapses (Kandel et al. (1982) Science 218:433-443; Bliss et al. (1993) Nature 361: 31-39). The molecular mechanisms for these changes are complex, involving many signal transduction pathways. Overall, however, these mechanisms are divided into two functionally distinct phases: induction, which initiates the long-term modifications, and maintenance, which sustains the changes (Malinow et al (1988) Nature 335:820-824; Schwartz, J. H. (1993) PNAS 90:8310-8313; Schwartz et al (1987) Ann. Rev. Neurosci. 10:459-476).

Much of the work to examine these signaling pathways has come from the study of the response to high-frequency afferent stimulation of synapses that causes a long-term increase in synaptic transmission, long-term potentiation (LTP) (Bliss et al. (1993), supra.; Bliss et al. (1973) J. Physiol. 232:331-356; Nicoll et al. (1988) 1:97-103). The vast majority of signaling molecules implicated in LTP affect only induction, but not maintenance. The exceptions are agents that inhibit the catalytic domain of protein kinases, specifically protein kinase C (PKC), which are able both to block LTP induction and reverse its maintenance. (Nishizuka, Y (1988) Nature 334:661-665; Schwartz, J. H. (1993) supra; Schwartz et al (1987) supra.

These two phases can be distinguished experimentally by the timing of the application of pharmacological agents that inhibit signal transduction pathways. When agents are applied prior to a tetanic afferent stimulation and prevent the formation of long-lasting changes, they block induction. If they are applied after the tetanus—and reverse the potentiation that has been established—they affect maintenance.

Several principles have been proposed to characterize mechanisms that might maintain long-term changes in synaptic transmission. First, protein kinases, such as PKC, which transiently enhance synaptic transmission when second messengers are activated, can extend their action by becoming constitutively active kinases that are independent of second messengers. (Schwartz et al (1987) supra; Klann et al. (1991) J. Biol. Chem. 266:24253-24256)

Second, long-term forms of synaptic plasticity are thought to depend upon new protein synthesis, although the critical, newly synthesized molecules that cause synaptic potentiation have not been identified. Stanton et al. (1984) J. Neurosci. 4:3080-3088; Frey et al (1988) Brain Res. 452:57-65; Otani et al (1989) Neurosci. 28: 519-526; Abel et al. (1998) Science 279: 338-341. A similar requirement for new protein synthesis has been observed for long-term memory. Davis et al. (1984) Psychol Bull. 96:518-559; Thompson, R. F. Science 233:941-947; Montarola et al. (1986) Science 234:1249-1254.

While usually considered properties of separate mechanisms, it has been determined that one isoform of PKC possesses both of these features: it is persistently increased during LTP as a constitutively active enzyme, and it is generated by new protein synthesis. Sacktor et al. (1993) Proc. Natl. Acad. Sci. (USA) 90:8342-8346. This newly described form of PKC is PKMζ, the independent catalytic domain of the PKCζ isoform, which, lacking PKCζ's autoinhibitory regulatory domain, is autonomously active. Schwartz, J. H. (1993) supra; Sacktor et al. (1993) supra.

PKM is usually thought to be produced by limited proteolysis of PKC, separating the enzyme's regulatory and catalytic domains. This may occur early after a high-frequency tetanus. Recent evidence shows, however, that the long-lasting PKMζ may also be derived from a brain-specific mRNA that encodes only the catalytic domain of ζ. Andrea et al. (1995) Biochem. J. 310:835-843; Powell et al. (1994) Cell Growth Differ. 5:143-149.

PKC is a family of multifunctional protein kinases, first discovered by Nishizuka in 1977. Takai et al. (1977) J. Biol. Chem. 252:7603-7609; Inoue et al. (1977) J. Biol. Chem. 252:7610-7616. PKC consists of two domains separated by a hinge region: an amino-terminal regulatory domain, which contains an autoinhibitory pseudosubstrate sequence and second messenger/lipid binding sites, and a carboxy-terminal catalytic kinase domain. PKC is held in an inactive state in the cytosol by the interaction between the regulatory and catalytic domains. When there is an increase in lipid second messengers (or, for some isoforms, $Ca^{2+}$), PKC translocates from the cytosolic to membranous (or cytoskeletal) compartments, and a change in its conformation occurs, displacing the regulatory from the catalytic domain, releasing the autoinhibition, and activating the enzyme. The 10 different forms of PKC are divided into 3 groups: conventional ($\alpha$, $\beta I$, $\beta II$, $\gamma$), novel (or new, $\delta$, $\epsilon$, $\eta$, $\theta$), and atypical ($\zeta$, $\iota/\lambda$), each of which is activated by a distinct set of second messengers. (PKD or PKCμ is a PKC-related molecule with a catalytic domain closer to CaM-kinase). The conventional PKCs are activated by $Ca^{2+}$ and diacylglycerol (DAG); the novel by DAG, but not $Ca^{2+}$ and the atypical by neither DAG or $Ca^{2+}$, but by alternate lipid-second messengers, including arachidonic acid, phosphoinositide 3-OH kinase products, and ceramide.

A second mechanism for permanently activating PKC, also discovered by Nishizuka, is the cleavage by calpain or their proteases at the hinge region, to permanently separate the regulatory from the catalytic domains. The independently active kinase domain is called PKM. ("M" stands for $Mg^{2+}$, although this requirement turned out to be for the $Mg^{2+}$ in $Mg^{2+}$-ATP). PKM formation results in a persistently active kinase and is not the typical way PKC is activated. It has been found that stable PKM formation occurs endogenously only for a single isoform, ζ, and only in brain. Naik et al. (submitted for publication). Recently, PKMζ has also been reported in a neuronally differentiated cell line. Oehrlein et al. (1998) Eur. J. Cell. Bio. 77:323-337.—Stable PKM forms for the other isoforms have been observed only in pathological conditions: PKMδ in breast cancer tumor cells (Baxter et al. (1992) J. Biol. Chem. 267: 1910-1917) and heart ischemia (Urthaler et al. (1997) Cardiovasc. Res. 35:60-67) and PKMζ in apoptosis (Emoto et al. (1996) Blood 97:1990-1996; Denning et al. (1998) J. Biol Chem. 273:29995-30002).

Protein kinase M zeta (PKMζ) is a form of protein kinase C which has a fundamental role in the formation and maintenance of memory. PKMζ is a critical molecule in the most widely-studied physiological model of memory, long-term potentiation (LTP) of synapses (Sacktor, et al., (1993) supra.; Osten, et al., (1996) J. Neurosci. 16(8):2444-2451; Hrabetova and Sacktor, (1996) J. Neurosci. 16(17):4324-5333).

SUMMARY OF THE INVENTION

The present invention provides methods and compositions for enhancing memory and treating brain and spinal cord injury by the administration of a therapeutically effective amount of one or more atypical forms of protein kinase C (PKC) such as PKMζ or PKC iota/lambda.

In one aspect, the present invention provides method of enhancing synaptic transmission in an animal comprising the administration of a therapeutically effective amount of one or more atypical forms of PKC such as PKMζ or PKC iota/lambda.

In another aspect, the present invention provides a method of maintaining memory in an animal comprising the administration of a therapeutically effective amount of one or more atypical forms of PKC such as PKMζ or PKC iota/lambda.

In still another aspect, the present invention provides a method for enhancing synaptic transmission or maintaining memory comprising the administration of DNA encoding the human (or animal) sequence of PKMζ. In yet another aspect, the present invention provides a method for causing amnesia or decreasing synaptic transmission, comprising the administration of a therapeutically effective amount of a PKMζ inhibitor. Uses for decreasing synaptic transmission include, for example, the treatment of acute or chronic pain, treatment of drug or alcohol addiction, and treatment of epilepsy.

In still yet another aspect, the present invention provides a method for causing amnesia or decreasing synaptic transmission, comprising the administration of a therapeutically effect amount of a dominant negative PKMζ inhibitor, DNA encoding the human (or animal) sequence of dominant negative PKMζ, or antisense to PKMζ.

In another aspect, the present invention provides a method of causing amnesia in an animal comprising the administration of a therapeutically effective amount of a PKMζ inhibitor or a PKC iota/lambda inhibitor.

In still another aspect, the present invention provides a pharmaceutical composition comprising PKMζ and a pharmaceutically acceptable carrier.

In yet another aspect, the present invention provides a pharmaceutical composition comprising PKC iota/lambda and a pharmaceutically acceptable carrier.

BRIEF DESCRIPTION OF THE DRAWINGS

FIG. 3 shows a silver stain of purified recombinantly expressed PKMζ.

FIG. 6 shows the DNA sequence (derived from cDNA) encoding human PKMζ.

DETAILED DESCRIPTION OF THE INVENTION

The present invention provides methods and compositions for enhancing memory and treating brain and spinal cord injury by the administration of a therapeutically effective amount of one or more atypical forms of PKC. In a preferred embodiment an atypical form of PKC is PKMζ. In another preferred embodiment an atypical form of PKC is PKC iota/lambda. In accordance with the present invention it has been determined that PKMζ is both necessary and sufficient for the long-term maintenance of LTP. Moreover, it has been determined in accordance with the present teachings that the function of PKMζ is to store and consolidate memories in the brain.

In accordance with the present invention, members of the class of compounds known as atypical forms of PKC such as protein kinase M zeta (PKMζ) and PKC iota/lambda have been found to maintain or consolidate long term changes in synaptic strength in vertebrates, the mechanism for long term memory. The present invention elucidates PKMζ's role in maintaining enhanced synaptic transmission with studies of long-term potentiation (LTP). Conversely, inhibition of PKMζ may cause amnesia, which may be useful in the treatment of traumatic stress disorders, phobias and acute or chronic pain.

Other agents that have been proposed to enhance memory are essentially stimulates (like coffee) or agents designed to enhance the induction of long-term potentiation (LTP)-like processes (such as drugs to increase cAMP). PKMζ is the first molecule whose function is to maintain memories in vertebrates. In accordance with the present invention, when PKMζ is injected into neurons it persistently enhances synaptic transmission.

In one embodiment the present invention contemplates a method of treating a brain injury in an animal comprising the administration of a therapeutically effective amount of one or more atypical forms of PKC such as PKMζ or DNA encoding PKMζ message. By therapeutically effective amount is meant an amount of an atypical form of PKC high enough to significantly positively modify the condition to be treated but low enough to avoid serious side effects (at a reasonable benefit/risk ratio), within the scope of sound medical judgment. For example, a therapeutically effective amount of PKMζ will vary with the particular injury being treated, the age and physical condition of the patient being treated, the severity of the injury, the duration of treatment, the nature of concurrent therapy and the specific PKMζ employed.

In another embodiment the present invention contemplates a method of treating a spinal cord injury in an animal comprising the administration of a therapeutically effective amount of one or more atypical forms of PKC such as, for example, PKMζ.

In still another embodiment, the present invention contemplates a method of enhancing synaptic transmission in an animal comprising the administration of a therapeutically effective amount of one or more atypical forms of PKC such as, for example, PKMζ.

Figure 5:
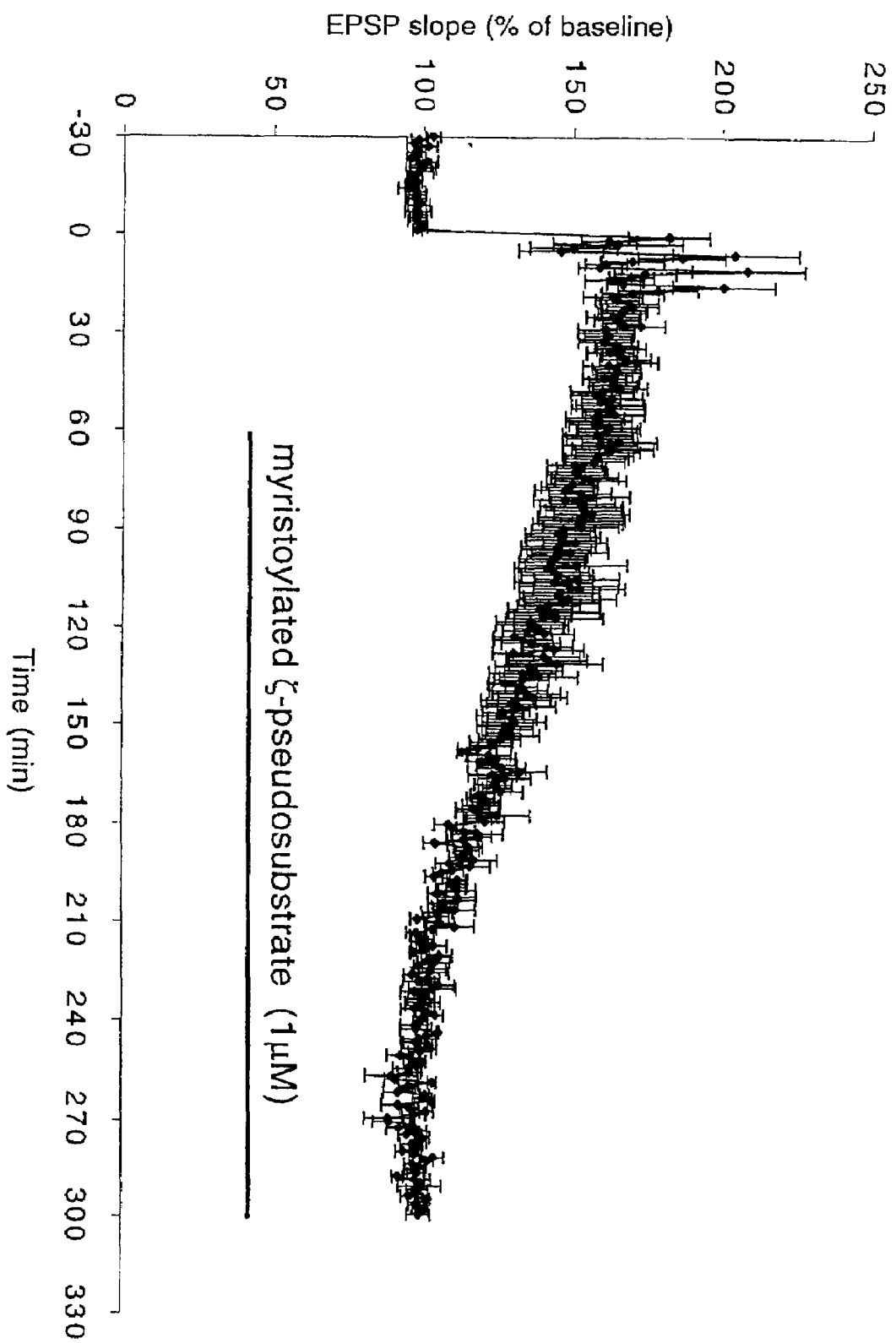
FIG. 5 shows that a myristolated zeta inhibitory pseudosubstrate peptide (1 μM), reverses LTP maintenance.

The present invention also contemplates a method of inducing amnesia in an animal by the administration of a therapeutically effective amount of a PKMζ inhibitor. In preferred embodiments the PKMζ inhibitor is chelerythrine, myristolated zeta inhibitory pseudosubstrate (MZIP) peptide (myr-Ser-Ile-Tyr-Arg-Arg-Gly-Ala-Arg-Arg-Trp-Arg-Lys-Leu-OH) (SEQ ID NO:4), or dominant negative form of PKMζ such as, for example, PKMζ-K281W, or antisense to PKMζ mRNA. MZIP has an IC50 of 10-100 nM for PKMζ and 10,000 nM for PKC gamma and therefore is a more specific inhibitor than chelerythrine (see FIG. 5). Candidates for the induction of selective amnesia contemplated by the present invention are preferably humans having, for example, post-traumatic stress disorders and phobias.

The present invention also contemplates a method of reducing synaptic transmission in selective areas of the brain or spinal cord by the administration of a therapeutically effective amount of PKMζ inhibitor. Candidates for the reduction of synaptic transmission contemplated by the invention are preferably humans having, for example, disorders of pain, drug or alcohol addiction, or excess neuronal activity as in epilepsy.

Still another embodiment of the present invention contemplates pharmaceutical compositions containing one or more atypical forms of PKC such as, for example, PKMζ.

The active ingredients of a pharmaceutical composition containing PKMζ or a nucleic acid encoding PKMζ is contemplated to exhibit effective therapeutic activity, for example, in enhancing memory, and treating brain and spinal cord injuries. Thus the active ingredients of the therapeutic compositions containing PKMζ is administered in therapeutic amounts which depend on the particular disease. For example, final concentrations of PKMζ in brain or spinal cord to be achieved by administration may be about 1 nanomolar. The dosage regimen may be adjusted to provide the optimum therapeutic response. For example, several divided doses may be administered daily or the dose may be proportionally reduced as indicated by the exigencies of the therapeutic situation. Administration of one or more atypical forms of PKC such as, for example, PKMζ into the brain or spinal cord may be intracranially or intrathecally, i.e., by intrathecal pump or repository. Depending on the route of administration, the active ingredients which comprise PKMζ may be required to be coated in a material to protect said ingredients from the action of acids and other natural conditions which may inactivate said ingredients.

For example, PKMζ may be administered in an adjuvant or in liposomes. Adjuvants contemplated herein include resorcinols, non-ionic surfactants such as polyoxyethylene oleyl ether and n-hexadecyl polyethylene ether. Liposomes include water-in-oil-in-water P40 emulsions as well as conventional liposomes.

Under ordinary conditions of storage and use, the preparations of the present invention contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of the active material calculated to produce the desired therapeutic effect in association with the required pharmaceutical carrier. The specification for the novel dosage unit forms of the invention are dictated by and directly depending on (a) the unique characteristics of the active material and the particular therapeutic effect to be achieved, and (b) the limitations inherent in the art of compounding such as active material for the treatment of injury in living subjects having a condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, result in achieving, for example, about 0.1 to about 10 nanomolar concentrations of PKMζ in the brain or spinal cord.

As used herein "pharmaceutically acceptable carrier" includes any and all solvents, dispersion media, coatings, antibacterial and antifungal agents, isotonic and adsorption delaying agents, and the like. The use of such media agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

Figures 2A, 2B:
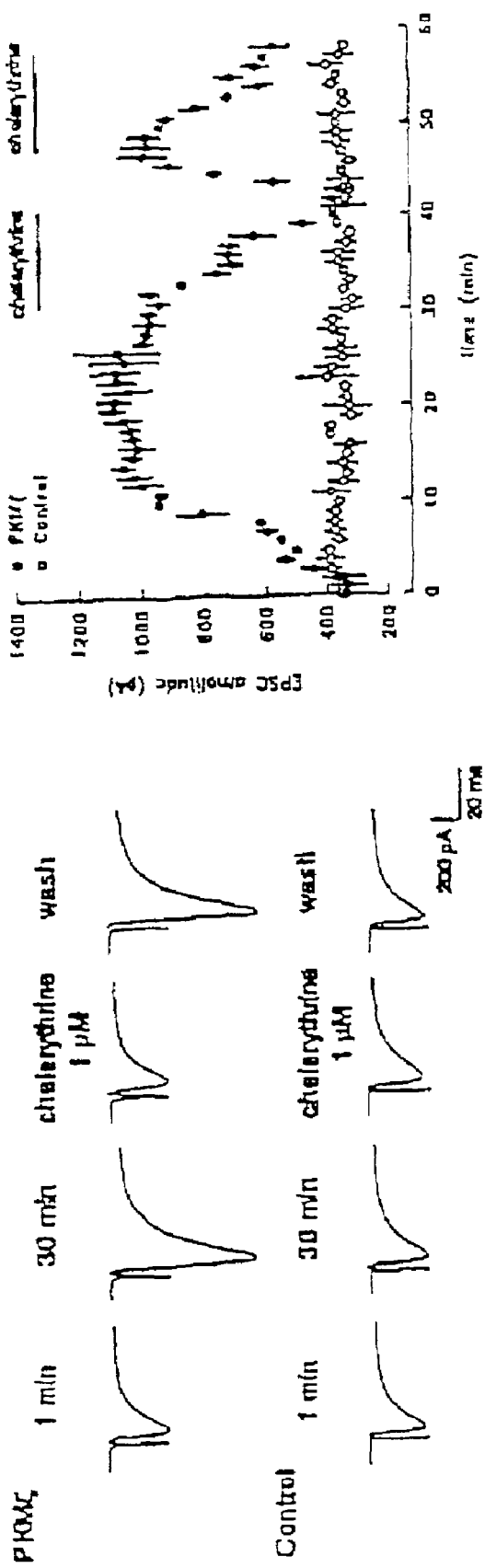
FIG. 2A shows whole cell recording of CA1 pyramidal cells with 3 nM PKM. Increases in synaptically evoked AMPA/kainate responses with the introduction of PKMζ were reversible by chelerythrine (1 uM).
FIG. 2B shows the time course of EPSC amplitudes.
Figure 4:
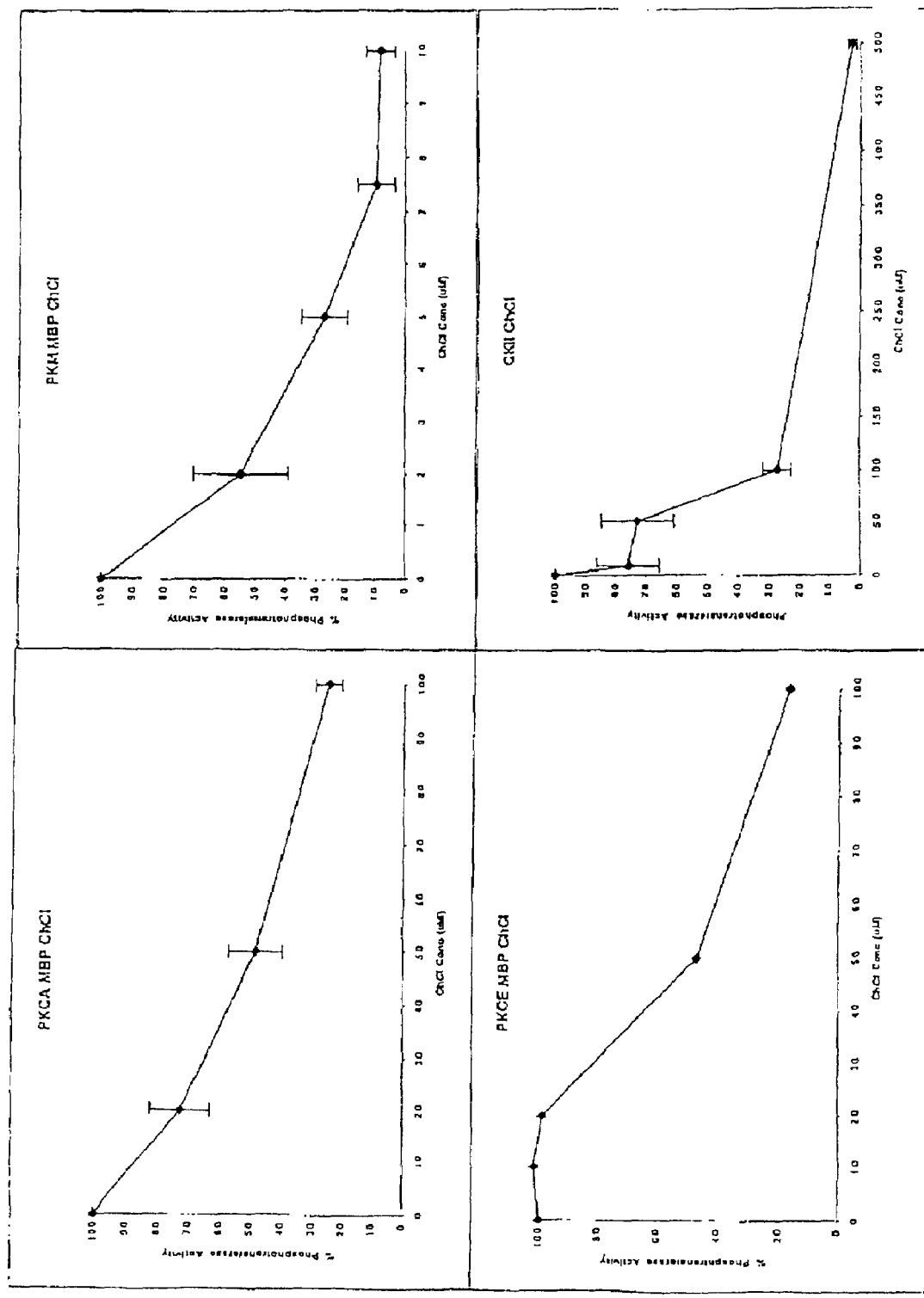
FIG. 4 shows specificity of inhibition of PKMζ relative to other protein kinases by chelerythrine. PKCA is PKC alpha phosphorylation of myelin basic protein (MBP). PKCE is PKC epsilon phosphorylation of MBP. PKM is PKMζ phosphorylation of MBP. CKII is $Ca^{2+}$-calmodulin-dependent protein kinase II phosphorylation of Syntide® (Calbiochem, San Diego, Calif.) peptide substrate.

Administration of an atypical form of PKC, such as PKMζ may also include altered forms or derivatives of PKMζ or drugs that enhance its activity, stability, or accessibility to the nervous system. The identification of applicable PKMζ enhancing drugs are readily tested or screened by examining the effects of drugs or PKMζ's phosphorylation in vitro (as measured in FIG. 4) or on PKMζ's effect on synaptic transmission when injected into neurons as in FIG. 2.

Administration of PKMζ DNA into brain or spinal cord may also be by gene-transfer technology. Such technologies include, but are not limited to, viruses, liposomes, and altered forms or derivatives of DNA or RNA.

Administration of inhibitors of PKMζ activity include drugs, such as chelerythrine, myristolated zeta inhibitory pseudosubstrate peptide and altered forms of PKMζ that, through dominant negative effects inhibit endogenous PKMζ's activity or effectiveness. Such dominant negative agents include, but are not limited to, inactive forms or portions of PKMζ. Inhibition of PKMζ function may also include decreasing levels of endogenous PKMζ through administration of antisense to the sequence of PKMζ.

The following Examples serve to further illustrate the invention without in any way limiting same.

EXAMPLE 1

The effect of the increase of PKMζ on synaptic transmission.

Intracellular Perfusion of PKMζ.

Figures 1A, 1B:
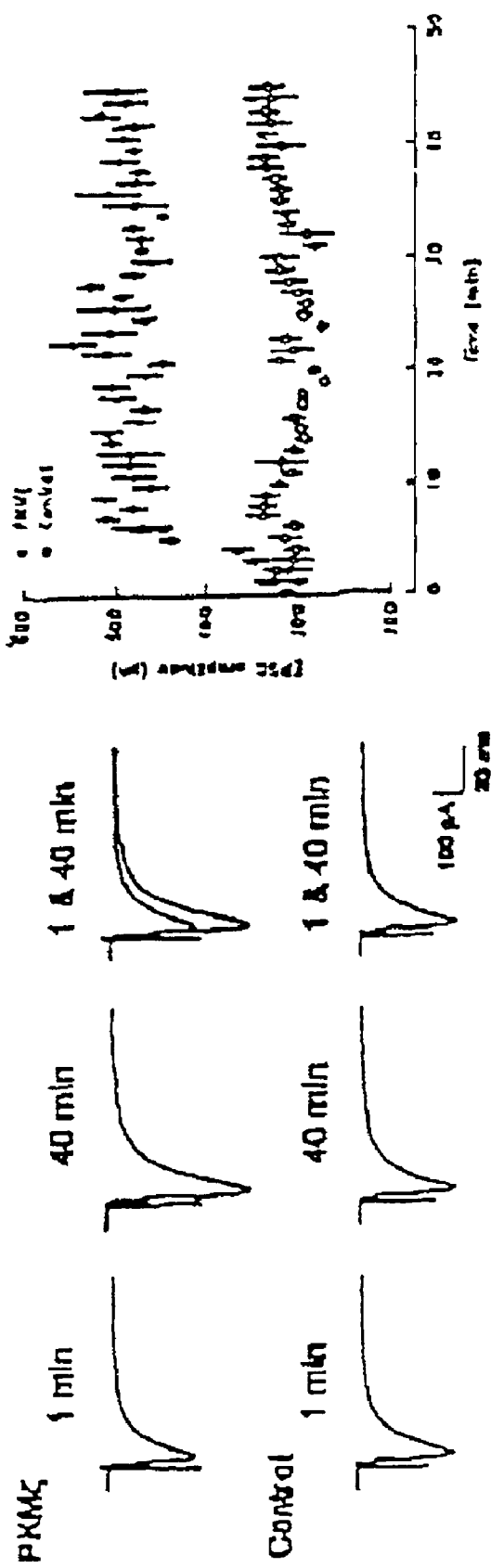
FIG. 1A shows individual EPSC responses to injected PKMζ.
FIG. 1B shows the time course of EPSC amplitudes.

PKMζ, purified from a baculovirus/Sf9 expression system to near homogeneity, was perfused into a CA1 pyramidal cell through a whole cell recording pipette (FIGS. 1A-1B). The concentration of PKMζ was about 0.8 nM PKMζ, with 0.03 pmol/min/μl activity. In order to isolate AMPA/kainate responses, the cell, recorded at the soma, was voltage-clamped at the IPSC reversal potential (~-70) and Cs-gluconate-based electrode solution was used (to block $GABA_B$ effects). Stimulation was every 10 sec in the radiatum, and input resistance was monitored and did not change throughout the experiment. Over 5-10 min, there was ~60% increase in AMPA/kainate EPSCs, which then stabilized. In contrast, inactivated PKMζ had no effect. In comparison with the concentration of autoactive thiophosphorylated CaM-kinase II reported to potentiate synaptic responses in CA1 pyramidal cells by similar whole cell techniques, the findings on the potentiation of AMPA/kainate currents indicated that PKMζ was 200- to 1000-fold more potent than CaM-kinase II.

Electrophysiological Recording.

Hippocampal slices were prepared from Sprague-Dawley rats as described in Example 2. Patch electrodes were pulled (two-stage) from 15 mm O.D. borosilicate glass (World Precision Instruments, Sarasota, Fla.) on a Narishige PP-83 vertical puller. Recording pipettes had tip resistances of 2-5 MΩ and contain (in mM): Cs-gluconate or K-gluconate 130-; $MgCl_2$, 2; $CaCl_2$, 2; EGTA, 10; HEPES, 10; Na-ATP, 2; pH adjusted to 7.25 with either CsOH or KOH. This mixture had been shown to reduce the rundown of $GABA_A$-receptor mediated responses. Cesium was used to block potassium currents, including slow $GABA_B$ IPSCs. Electrode solutions included QX-314 (10 mM) to block $Na^{2+}$ currents to prevent cell spike discharges at depolarized holding potentials. Whole-cell recordings were obtained from CA1 pyramidal cells using blind patch techniques. The recording pipette was slowly advanced through the tissue, with brief voltage steps (−10 mV, 10 ms) applied to monitor electrode resistance. Once a deflection in the electrode's current response was detected signifying contact with the membrane of the target cell soma, slight negative pressure was applied to form a cell-electrode seal of >1 GΩ.

Membrane breakthrough was accomplished with either additional suction or current pulses. Following membrane rupture, 2 min of settling time was allowed before formal recording. Voltage steps (−10 mV) were applied to monitor the access resistance and input capacitance. Signals were recorded under voltage-clamp with an Axoclamp 2A amplifier (Axon Instruments, Foster City, Calif.). Resting input resistance was measured from the current response to a −10 mV voltage step from holding potential. (usually resting membrane potential, 60 mV with the intracellular solution). Cells were accepted for study only if resting input resistances of >100 MΩ and access resistances <20 MΩ were observed.

If cell access resistance increased significantly during the course of the recording (>20%), the data was discarded. Data signals were digitized at 94 kHz via a 14-bit PCM interface (VR-10B Digital Data Recorder, Instrutech Corp., Element, N.Y.) and stored on VHS tape for later analysis with pCLAMP software (Axon Instruments) on an IBM-compatible Pentium-II microcomputer.

Synaptic events were evoked by extracellular stimulation with bipolar, coated tungsten electrodes placed in stratum radiatum lateral to the recording electrode. Cathodal shocks (2-10 V; 200 us duration) were delivered through a digitally controlled stimulus isolation unit (World Precision Instruments) at a low frequency (0.1 Hz). Unless otherwise noted, drugs were delivered in the bath.

EXAMPLE 2

Methods: Preparation of hippocampal slices. After anesthesia with halothane, transverse 450 μm slices were prepared from 3-4 week old Sprague-Dawley rats with a McIlwain tissue chopper. During the dissection, the hippocampus was kept cold with multiple washes of a dissection saline at 4° C. (125 mM NaCl, 2.5 mM KCl, 1.25 mM $NaH_2PO_4$, 26 mM $NaHCO_3$, 11 mM glucose, 10 mM $MgCl_2$ and 0.5 mM $CaCl_2$, pH 7.4, equilibrated with 95% $O_2$/5% $CO_2$). The slices were transferred to an interface chamber (Fine Science Tools) for incubation in the dissection saline for 1 hour at 32° C. The divalent ion concentrations were then changed to 1.2 mM MgCl$_2$ and 1.7 mM CaCl$_2$ (physiological saline).

Intracellular Perfusion of PKMζ.

Analysis of the Effect of PKMζ on Evoked EPSCs in CA1 Pyramidal Neurons and Effects of Chelerythrine.

The effects of PKMζ cell injection on excitatory synaptic currents were assessed by including the kinase in the whole-cell pipette and measuring EPSC amplitude over time. Synaptic events were recorded in the soma of hippocampal CA1 pyramidal cells with Cs-gluconate-based electrode solutions containing varying concentrations of PKMζ (0.1, 1, 10 nM). With cells voltage-clamped at the IPSC reversal potential ($E_{ipsc}$ ~-70 mV), isolated ensemble EPSCs were elicited by low-frequency (0.1 Hz) electrical stimulation applied in stratum radiatum. Stimulus intensity was set at moderate levels (~5 V) to selectively evoke fast EPSCs (i.e., AMPA/kainate-mediated) and was held constant throughout the experiment. Control data consisted of measurements of EPSC amplitude and duration immediately following establishment of a whole-cell recording (i.e., before PKMζ diffusion into the target cell), and parallel experiments with the kinase denatured by boiling or inactivated by multiple freeze/thaw. Activity of the perfused PKMζ was determined by phosphorylation assay in vitro with each experiment.

EPSCs was continuously monitored to assess the effects of intracellular PKMζ on peak EPSC magnitude and duration. Periodically, current-voltage records were taken to check constancy of the PESC reversal potential ($E_{EPSC}$), and the input resistance of the cell was monitored throughout the experiment. Application of the non-NMDA-receptor antagonist CNQX (10 μM) was applied to slices to confirm that EPSCs elicited at $E_{IPSC}$ with moderate stimulus intensity were mediated solely through non-NMDA receptors.

Once an effect was observed and appeared stable, the competitive PKC catalytic domain inhibitor, chelerythrine, was added to the bath to attempt to reverse the effect by preventing PKMζ's phosphorylation. The drug was then washed out. An example of an experiment with chelerythrine using 3 nM PKMζ is provided in FIGS. 2A-2B.

EXAMPLE 3

Figure 3:
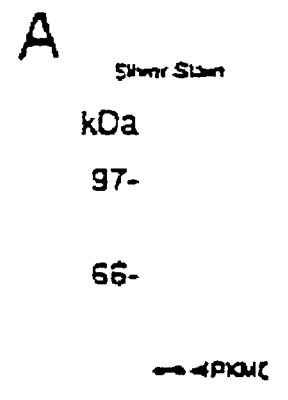

Purification of baculovirus-expressed PKMζ from Sf9 cells: *Spodoptera frugiperda* (Sf9) cells were grown in SF-900 II SFM insect cell culture medium (Gibco) containing 5 μg/ml gentamicin. To express the PKMζ, 10×10$^8$ cells of a healthy, log phase Sf-9 culture were spun, resuspended in 125 ml of medium, and infected with 25 ml of the baculovirus-ζ virus stock (gift of Sylvia Stable). Following a 0.5 hr incubation at room temperature, additional medium was added to the cells, which were then seeded at a density of 1×10$^6$ cells/ml. After 3 days, the cells were spun, washed with PBS, and then homogenized in 65 ml of homogenization buffer. A 2-step purification, employing DEAE Fast Flow Sepharose and Superdex 75 (preparation grade, Pharmacia) columns, was performed to purify baculovirus-expressed PKMζ. Activity of the PKMζ was assayed on the same day as each whole cell experiment. Silver stain of baculovirus, recombinantly expressed PKMζ showing purity of preparation. (See FIG. 3)

EXAMPLE 4

Specificity of Chelerythrine as Inhibitor of PKMζ

Inhibition by the drug chelerythrine of phosphorylation of exogenous substrates by various protein kinases showed that chelerythrine was greater than 10-fold selective as an inhibitor of PKM activity. (See FIG. 4).

EXAMPLE 5

Sense, Antisense, and Amino-Acid Sequence of Human PKMζ

Human sequence, obtained from published expressed sequence tags, were obtained by analogy with rat sequence (Ono, et al., 1988), which was identified as containing the open reading frame of PKMζ. The PKMζ sequence is used for gene transfer technology to increase levels of PKMζ in the nervous system. Dominant negative inhibitors of PKMζ are obtained by changing or deleting sequences in the ATP-binding site or by administering selective domains of the protein, e.g., the carboxy-terminal domain.

Dominant negative PKMζ was obtained by elimination or alteration of ATP-binding domain (marked), and by administration of carboxy-terminal domain (marked). Antisense was achieved by administration of all or part of antisense sequence to PKMζ. (See FIG. 6).

EXAMPLE 6

Figure 7:
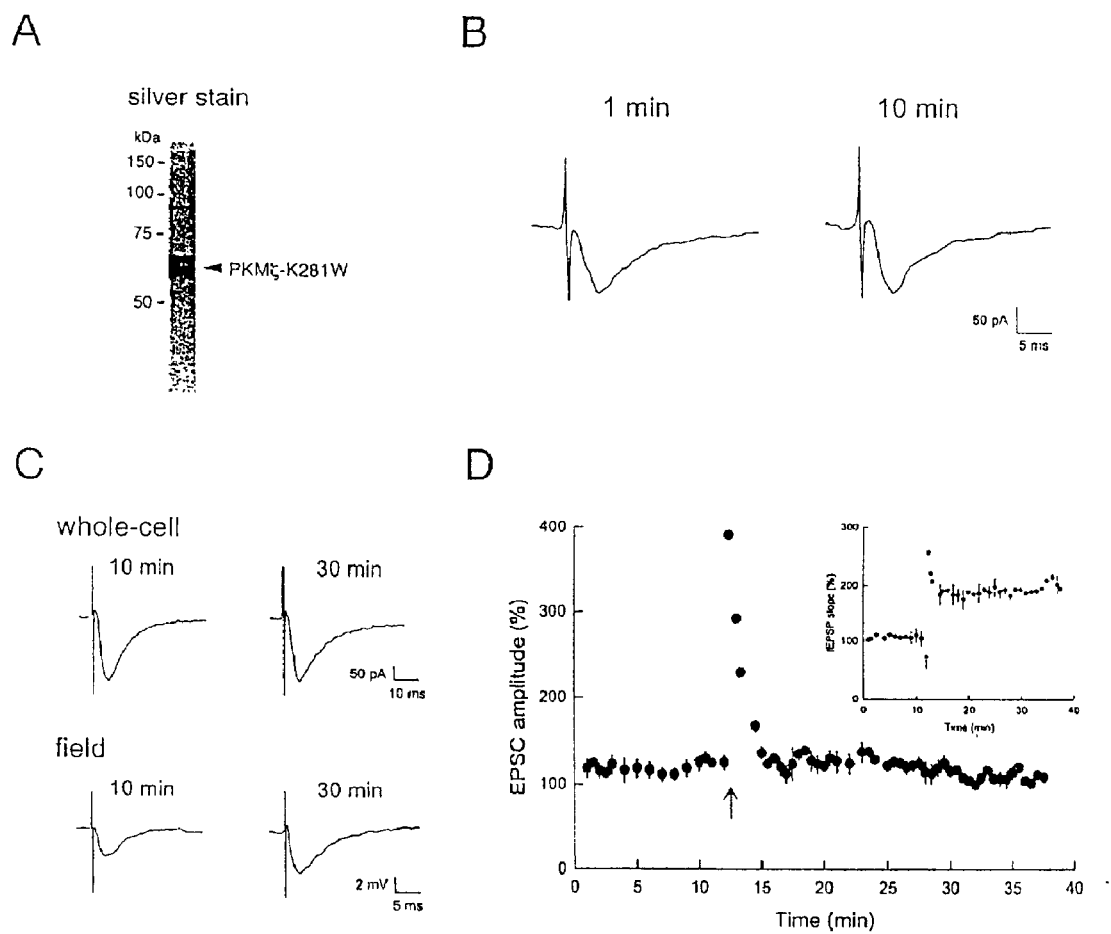
FIG. 7 shows postsynaptic exposure to dominant negative inhibitor PKMζ-K281W (20 nM) prevents LTP. (A) Silver stain of baculovirus/Sf9-expressed PKMζ-K281W protein placed into whole-cell recording pipette. PKMζ-K281W appears as a doublet. (B) Depolarization to −40 mV at 1 and 10 min after diffusion of PKMζ-K281W shows no obvious effect on synaptic responses mediated by AMPA and NMDA receptors. (C) Upper traces, whole-cell EPSCs pre- and post-tetanization, showing no persistent potentiation after exposure to PKMζ-K281W. Lower traces, simultaneously recorded field potentials show LTP. (D) Time course of whole-cell recording with PKMζ-K281W. Tetahization shows only PTP. Inset, time course of simultaneous field recordings shows LTP.

In order to confirm that PKMζ mediates potentiation of synaptic transmission during LTP, a dominant negative inhibitory form of PKMζ (PKMζ-K281W) was introduced postsynaptically into a CA1 pyramidal cell its effect on LTP was examined. The lysine$^{281}$ to tryptophan mutation in the catalytic domain of PKMζ-K281W) abolished kinase activity by disrupting ATP-binding. Twenty nanomolar of the dominant negative inhibitor (FIG. 7A) was included in a whole-cell recording pipette and allowed to diffuse for 10 min into a CA1 pyramidal cell, voltage clamped at -75 mV to isolated synaptic AMPA responses. PKMζ-K281W had no obvious effect on synaptic transmission mediated by AMPA and NMDA receptors, sampled at -40 mV at 1 min and 10 min (FIG. 7B). PKMζ-K281W completely eliminated persistent synaptic potentiation in the cell, but not post-tetanic potentiation (PTP) (FIG. 7C, upper traces, D, large graph). Twenty minutes after the tetanic stimulation, the EPSCs were 101.6±1.9% of baseline responses (n=4). Simultaneous LTP in the field responses of the slice was observed (FIG. 7C, lower traces, and D, inset graph).

PKMζ-K281W was expressed using the MaxBac 2.0 Baculovirus/Sf9 system (Invitrogen, Carlsbad, Calif.). An insert containing amino acids 158-592 of PKCζ (Drier, et al. (2000) 30$^{th}$ Annual Meeting of the Society of Neuroscience, New Orleans, La., generous gift from Jerry Yin, Cold Spring Harbor Laboratory, Cold Spring Harbor, N.Y.) was subcloned into the baculovirus transfer vector pBlueBacHis2B between the EcoRI and SalI sites. The construct was sequenced for verification, and then cotransfected into Sf9 cells with linearized baculovirus genome. Recombinant protein was expressed in Sf9 cells, and purified using a Ni$^{2+}$ column (Invitrogen, Xpress™ Purification Kit, Carlsbad, Calif.), and analyzed by silver stain (FIG. 7A) and Western blot (data not shown).

What is claimed is:

1. A method of enhancing memory in an animal comprising the administration of a therapeutically effective amount of protein kinase M zeta (PKMζ) intracranially or intrathecally, wherein the amino acid sequence of PKMζ is set forth as SEQ ID NO:2.

2. The method of claim 1 wherein said PKMζ is administered in an amount resulting in final concentrations of said PKMζ in brain ranging from about 0.1 to about 10 nanomolar.

3. A method of maintaining memory in an animal comprising the administration of a therapeutically effective amount of PKMζ intracranially or intrathecally.

4. The method of any one of claims 1, 2 3, wherein said animal is a human.

* * * * *

SEQUENCE LISTING

<160> NUMBER OF SEQ ID NOS: 4

<210> SEQ ID NO 1
<211> LENGTH: 2058
<212> TYPE: DNA
<213> ORGANISM: Homo sapiens
<220> FEATURE:
<221> NAME/KEY: CDS
<222> LOCATION: (444)..(1670)
<220> FEATURE:
<221> NAME/KEY: unsure
<222> LOCATION: (522)
<223> OTHER INFORMATION: r at position 522 is g or a

<400> SEQUENCE: 1

```
cccgggcctg agacatgag gaggcaggga tgtgaggggc ggggacagg acagccggcc      60 ttccgttaaa tatctgctcc tcgcgctcga gcctccctgc ctattgtcgg ggccggagcg    120
aagccgacgc agcatcagct cgtcaacggg aaggaagatg cctccctgca cgcccgccgc    180
gcacagagca taaagaatct gcgctgagga ggcaggagaa gaaagccgaa tctatctacc    240
gccggggagc cagaagatgg aggaagctgt accgtgccaa cggccacctc ttccaagcca    300
agcgctttaa caggagagcg tactgcggtc agtgcagcga gaggatatgg ggcctcgcga    360
ggcaaggcta caggtgcatc aactgcaaac tgctggtcca taagcgctgc cacggcctcg    420
tcccgctgac ctgcaggaag cat atg gat tct gtc atg cct tcc caa gag cct    473
                          Met Asp Ser Val Met Pro Ser Gln Glu Pro
                           1               5                   10 cca gta gac gac aag aac gag gac gcc gac ctt cct tcc gag gag aca      521
Pro Val Asp Asp Lys Asn Glu Asp Ala Asp Leu Pro Ser Glu Glu Thr
                15                  20                  25 rat gga att gct tac att tcc tca tcc cgg aag cat gac agc att aaa      569
Xaa Gly Ile Ala Tyr Ile Ser Ser Ser Arg Lys His Asp Ser Ile Lys
            30                  35                  40 gac gac tcg gag gac ctt aag cca gtt atc gat ggg atg gat gga atc      617
Asp Asp Ser Glu Asp Leu Lys Pro Val Ile Asp Gly Met Asp Gly Ile
        45                  50                  55 aaa atc tct cag ggg ctt ggg ctg cag gac ttt gac cta atc aga gtc      665
Lys Ile Ser Gln Gly Leu Gly Leu Gln Asp Phe Asp Leu Ile Arg Val
    60                  65                  70 atc ggg cgc ggg agc tac gcc aag gtt ctc ctg gtg cgg ttg aag aag      713
Ile Gly Arg Gly Ser Tyr Ala Lys Val Leu Leu Val Arg Leu Lys Lys
75                  80                  85                  90 aat gac caa att tac gcc atg aaa gtg gtg aag aaa gag ctg gtg cat      761
Asn Asp Gln Ile Tyr Ala Met Lys Val Val Lys Lys Glu Leu Val His
                95                  100                 105 gat gac gag gat att gac tgg gta cag aca gag aag cac gtg ttt gag      809
Asp Asp Glu Asp Ile Asp Trp Val Gln Thr Glu Lys His Val Phe Glu
            110                 115                 120 cag gca tcc agc aac ccc ttc ctg gtc gga tta cac tcc tgc ttc cag      857
Gln Ala Ser Ser Asn Pro Phe Leu Val Gly Leu His Ser Cys Phe Gln
        125                 130                 135 acg aca agt cgg ttg ttc ctg gtc att gag tac gtc aac ggc ggg gac      905
Thr Thr Ser Arg Leu Phe Leu Val Ile Glu Tyr Val Asn Gly Gly Asp
    140                 145                 150 ctg atg ttc cac atg cag agg cag agg aag ctc cct gag gag cac gcc      953
Leu Met Phe His Met Gln Arg Gln Arg Lys Leu Pro Glu Glu His Ala
155                 160                 165                 170 agg ttc tac gcg gcc gag atc tgc atc gcc ctc aac ttc ctg cac gag     1001
Arg Phe Tyr Ala Ala Glu Ile Cys Ile Ala Leu Asn Phe Leu His Glu
```

-continued

```
                   175                 180                 185
agg ggg atc atc tac agg gac ctg aag ctg gac aac gtc ctc ctg gat    1049
Arg Gly Ile Ile Tyr Arg Asp Leu Lys Leu Asp Asn Val Leu Leu Asp
            190                 195                 200 gcg gac ggg cac atc aag ctc aca gac tac ggc atg tgc aag gaa ggc    1097
Ala Asp Gly His Ile Lys Leu Thr Asp Tyr Gly Met Cys Lys Glu Gly
        205                 210                 215 ctg ggc cct ggt gac aca acg agc act ttc tgc gga acc ccg aat tac    1145
Leu Gly Pro Gly Asp Thr Thr Ser Thr Phe Cys Gly Thr Pro Asn Tyr
    220                 225                 230 atc gcc ccc gaa atc ctg cgg gga gag gag tac ggg ttc agc gtg gac    1193
Ile Ala Pro Glu Ile Leu Arg Gly Glu Glu Tyr Gly Phe Ser Val Asp
235                 240                 245                 250 tgg tgg gcg ctg gga gtc ctc atg ttt gag atg atg gcc ggg cgc tcc    1241
Trp Trp Ala Leu Gly Val Leu Met Phe Glu Met Met Ala Gly Arg Ser
                255                 260                 265 ccg ttc gac atc atc acc gac aac ccg gac atg aac aca gag gac tac    1289
Pro Phe Asp Ile Ile Thr Asp Asn Pro Asp Met Asn Thr Glu Asp Tyr
            270                 275                 280 ctt ttc caa gtg atc ctg gag aag ccc atc cgg atc ccc cgg ttc ctg    1337
Leu Phe Gln Val Ile Leu Glu Lys Pro Ile Arg Ile Pro Arg Phe Leu
        285                 290                 295 tcc gtc aaa gcc tcc cat gtt tta aaa gga ttt tta aat aag gac ccc    1385
Ser Val Lys Ala Ser His Val Leu Lys Gly Phe Leu Asn Lys Asp Pro
    300                 305                 310 aaa gag agg ctc ggc tgc cgg cca cag act gga ttt tct gac atc aag    1433
Lys Glu Arg Leu Gly Cys Arg Pro Gln Thr Gly Phe Ser Asp Ile Lys
315                 320                 325                 330 tcc cac gcg ttc ttc cgc agc ata gac tgg gac ttg ctg gag aag aag    1481
Ser His Ala Phe Phe Arg Ser Ile Asp Trp Asp Leu Leu Glu Lys Lys
                335                 340                 345 cag gcg ctc cct cca ttc cag cca cag atc aca gac gac tac ggt ctg    1529
Gln Ala Leu Pro Pro Phe Gln Pro Gln Ile Thr Asp Asp Tyr Gly Leu
            350                 355                 360 gac aac ttt gac aca cag ttc acc agc gag ccc gtg cag ctg acc cca    1577
Asp Asn Phe Asp Thr Gln Phe Thr Ser Glu Pro Val Gln Leu Thr Pro
        365                 370                 375 gac gat gag gat gcc ata aag agg atc gac cag tca gag ttc gaa ggc    1625
Asp Asp Glu Asp Ala Ile Lys Arg Ile Asp Gln Ser Glu Phe Glu Gly
    380                 385                 390 ttt gag tat atc aac cca tta ttg ctg tcc acc gag gag tcg gtg         1670
Phe Glu Tyr Ile Asn Pro Leu Leu Leu Ser Thr Glu Glu Ser Val
395                 400                 405 tgaggccgcg tgcgtctctg tcgtggacac gcgtgattga cccttttaact gtatccttaa  1730 ccaccgcata tgcatgccag gctgggcacg gctccgaggg cggccaggga cagacgcttg   1790
cgccgagacc gcagagggaa gcgtcagcgg gcgctgctgg gagcagaaca gtccctcaca   1850
cctggcccgg caggcagctt cgtgctggag gaacttgctg ctgtgcctgc gtcgcggcgg   1910
atccgcgggg accctgccga gggggctgtc atgcggtttc caaggtgcac attttccacg   1970
gaaacagaac tcgatgcact gacctgctcc gccaggaaag tgagcgtgta gcgtcctgag   2030
gaataaaatg ttccgatgaa aaaaaaaa                                     2058
```

<210> SEQ ID NO 2
<211> LENGTH: 409
<212> TYPE: PRT
<213> ORGANISM: Homo sapiens
<220> FEATURE:
<221> NAME/KEY: unsure
<222> LOCATION: (27)
<223> OTHER INFORMATION: Xaa at position 27 is Asp or Asn

<400> SEQUENCE: 2

```
Met Asp Ser Val Met Pro Ser Gln Glu Pro Val Asp Asp Lys Asn
  1               5                  10                  15

Glu Asp Ala Asp Leu Pro Ser Glu Glu Thr Xaa Gly Ile Ala Tyr Ile
              20                  25                  30

Ser Ser Ser Arg Lys His Asp Ser Ile Lys Asp Asp Ser Glu Asp Leu
          35                  40                  45

Lys Pro Val Ile Asp Gly Met Asp Gly Ile Lys Ile Ser Gln Gly Leu
 50                  55                  60

Gly Leu Gln Asp Phe Asp Leu Ile Arg Val Ile Gly Arg Gly Ser Tyr
 65                  70                  75                  80

Ala Lys Val Leu Leu Val Arg Leu Lys Lys Asn Asp Gln Ile Tyr Ala
                  85                  90                  95

Met Lys Val Val Lys Lys Glu Leu Val His Asp Asp Glu Asp Ile Asp
                 100                 105                 110

Trp Val Gln Thr Glu Lys His Val Phe Glu Gln Ala Ser Ser Asn Pro
                 115                 120                 125

Phe Leu Val Gly Leu His Ser Cys Phe Gln Thr Thr Ser Arg Leu Phe
130                 135                 140

Leu Val Ile Glu Tyr Val Asn Gly Gly Asp Leu Met Phe His Met Gln
145                 150                 155                 160

Arg Gln Arg Lys Leu Pro Glu Glu His Ala Arg Phe Tyr Ala Ala Glu
                 165                 170                 175

Ile Cys Ile Ala Leu Asn Phe Leu His Glu Arg Gly Ile Ile Tyr Arg
                 180                 185                 190

Asp Leu Lys Leu Asp Asn Val Leu Leu Asp Ala Asp Gly His Ile Lys
                 195                 200                 205

Leu Thr Asp Tyr Gly Met Cys Lys Glu Gly Leu Gly Pro Gly Asp Thr
                 210                 215                 220

Thr Ser Thr Phe Cys Gly Thr Pro Asn Tyr Ile Ala Pro Glu Ile Leu
225                 230                 235                 240

Arg Gly Glu Glu Tyr Gly Phe Ser Val Asp Trp Trp Ala Leu Gly Val
                 245                 250                 255

Leu Met Phe Glu Met Met Ala Gly Arg Ser Pro Phe Asp Ile Ile Thr
                 260                 265                 270

Asp Asn Pro Asp Met Asn Thr Glu Asp Tyr Leu Phe Gln Val Ile Leu
                 275                 280                 285

Glu Lys Pro Ile Arg Ile Pro Arg Phe Leu Ser Val Lys Ala Ser His
                 290                 295                 300

Val Leu Lys Gly Phe Leu Asn Lys Asp Pro Lys Glu Arg Leu Gly Cys
305                 310                 315                 320

Arg Pro Gln Thr Gly Phe Ser Asp Ile Lys Ser His Ala Phe Phe Arg
                 325                 330                 335

Ser Ile Asp Trp Asp Leu Leu Glu Lys Lys Gln Ala Leu Pro Pro Phe
                 340                 345                 350

Gln Pro Gln Ile Thr Asp Asp Tyr Gly Leu Asp Asn Phe Asp Thr Gln
                 355                 360                 365

Phe Thr Ser Glu Pro Val Gln Leu Thr Pro Asp Asp Glu Asp Ala Ile
                 370                 375                 380

Lys Arg Ile Asp Gln Ser Glu Phe Glu Gly Phe Glu Tyr Ile Asn Pro
385                 390                 395                 400
```

Leu Leu Leu Ser Thr Glu Glu Ser Val
          405

<210> SEQ ID NO 3
<211> LENGTH: 2058
<212> TYPE: DNA
<213> ORGANISM: Homo sapiens

<400> SEQUENCE: 3

| | | | | | |
|---|---|---|---|---|---|
| gggcccggac | ctctgtactc | ctccgtccct | acactcccg | cccctgtcc | tgtcggccgg | 60 |
| aaggcaattt | atagacgagg | agcgcgagct | cggaggacg | ataacagcc | ccggcctcgc | 120 |
| ttcggctgcg | tcgtagtcga | gcagttgccc | ttccttctac | ggagggacgt | gcgggcggcg | 180 |
| cgtgtctcgt | atttcttaga | cgcgactcct | ccgtcctctt | ctttcggctt | agatagatgg | 240 |
| cggcccctcg | gtcttctacc | tccttcgaca | tggcacggtt | gccggtggag | aaggttcggt | 300 |
| tcgcgaaatt | gtcctctcgc | atgacgccag | tcacgtcgct | ctcctatacc | ccggagcgct | 360 |
| ccgttccgat | gtccacgtag | ttgacgtttg | acgaccaggt | attcgcgacg | gtgccggagc | 420 |
| agggcgactg | gacgtccttc | gtatacctaa | gacagtacgg | aagggttctc | ggaggtcatc | 480 |
| tgctgttctt | gctcctgcgg | ctggaaggaa | ggctcctctg | tctaccttaa | cgaatgtaaa | 540 |
| ggagtagggc | cttcgtactg | tcgtaatttc | tgctgagcct | cctggaattc | ggtcaatagc | 600 |
| taccctacct | accttagttt | tagagagtcc | ccgaacccga | cgtcctgaaa | ctggattagt | 660 |
| ctcagtagcc | cgcgccctcg | atgcggttcc | aagaggacca | cgccaacttc | ttcttactgg | 720 |
| tttaaatgcg | gtactttcac | cacttctttc | tcgaccacgt | actactgctc | ctataactga | 780 |
| cccatgtctg | tctcttcgtg | cacaaactcg | tccgtaggtc | gttggggaag | gaccagccta | 840 |
| atgtgaggac | gaaggtctgc | tgttcagcca | acaaggacca | gtaactcatg | cagttgccgc | 900 |
| ccctggacta | caaggtgtac | gtctccgtct | ccttcgaggg | actcctcgtg | cggtccaaga | 960 |
| tgcgccggct | ctagacgtag | cgggagttga | aggacgtgct | ctcccctag | tagatgtccc | 1020 |
| tggacttcga | cctgttgcag | gaggacctac | gcctgcccgt | gtagttcgag | tgtctgatgc | 1080 |
| cgtacacgtt | ccttccggac | ccgggaccac | tgtgttgctc | gtgaaagacg | ccttggggct | 1140 |
| taatgtagcg | ggggctttag | gacgcccctc | tcctcatgcc | caagtcgcac | ctgaccaccc | 1200 |
| gcgaccctca | ggagtacaaa | ctctactacc | ggcccgcgag | gggcaagctg | tagtagtggc | 1260 |
| tgttgggcct | gtacttgtgt | ctcctgatgg | aaaaggttca | ctaggacctc | ttcgggtagg | 1320 |
| cctaggggc | caaggacagg | cagtttcgga | gggtacaaaa | ttttcctaaa | aatttattcc | 1380 |
| tggggtttct | ctccgagccg | acggccggtg | tctgacctaa | aagactgtag | ttcagggtgc | 1440 |
| gcaagaaggc | gtcgtatctg | accctgaacg | acctcttctt | cgtccgcgag | ggaggtaagg | 1500 |
| tcggtgtcta | gtgtctgctg | atgccagacc | tgttgaaact | gtgtgtcaag | tggtcgctcg | 1560 |
| ggcacgtcga | ctgggtctg | ctactcctac | ggtatttctc | ctagctggtc | agtctcaagc | 1620 |
| ttccgaaact | catatagttg | ggtaataacg | acaggtggct | cctcagccac | actccggcgc | 1680 |
| acgcagagac | agcacctgtg | cgcactaact | gggaaattga | cataggaatt | ggtggcgtat | 1740 |
| acgtacggtc | cgaccccgtgc | cgaggctccc | gccggtccct | gtctgcgaac | gcggctctgg | 1800 |
| cgtctcccctt | cgcagtcgcc | cgcgacgacc | ctcgtcttgt | cagggagtgt | ggaccgggcc | 1860 |
| gtccgtcgaa | gcacgaccctc | cttgaacgac | gacacggacg | cagcgccgcc | taggcgcccc | 1920 |
| tgggacggct | ccccgacag | tacgccaaag | gttccacgtg | taaaaggtgc | ctttgtcttg | 1980 |
| agctacgtga | ctggacgagg | cggtcctttc | actcgcacat | cgcaggactc | cttatttttac | 2040 |

```
aaggctactt tttttttt                                                  2058

<210> SEQ ID NO 4
<211> LENGTH: 13
<212> TYPE: PRT
<213> ORGANISM: Unknown Organism
<220> FEATURE:
<223> OTHER INFORMATION: Description of Unknown Organism: mzip peptide

<400> SEQUENCE: 4

Ser Ile Tyr Arg Arg Gly Ala Arg Arg Trp Arg Lys Leu
 1               5                   10
```